US011350918B2

(12) United States Patent
Cawthon

(10) Patent No.: US 11,350,918 B2
(45) Date of Patent: Jun. 7, 2022

(54) NON-CLOGGING DISPENSING DEVICE

(71) Applicants: BAXTER INTERNATIONAL INC., Deerfield, IL (US); BAXTER HEALTHCARE SA, Glattpark (CH)

(72) Inventor: Dustin Christopher Cawthon, Crystal Lake, IL (US)

(73) Assignees: BAXTER INTERNATIONAL INC., Deerfield, IL (US); BAXTER HEALTHCARE SA, Glattpark (CH)

( * ) Notice: Subject to any disclaimer, the term of this patent is extended or adjusted under 35 U.S.C. 154(b) by 409 days.

(21) Appl. No.: 16/607,011

(22) PCT Filed: Apr. 18, 2018

(86) PCT No.: PCT/US2018/028109
§ 371 (c)(1),
(2) Date: Oct. 21, 2019

(87) PCT Pub. No.: WO2018/195161
PCT Pub. Date: Oct. 25, 2018

(65) Prior Publication Data
US 2020/0245989 A1 Aug. 6, 2020

Related U.S. Application Data

(60) Provisional application No. 62/487,261, filed on Apr. 19, 2017.

(51) Int. Cl.
*A61B 17/00* (2006.01)
(52) U.S. Cl.
CPC ............ *A61B 17/00491* (2013.01); *A61B 2017/0096* (2013.01); *A61B 2017/00495* (2013.01)

(58) Field of Classification Search
CPC .... A61B 17/00495; A61B 2017/00522; A61B 17/00491; B05B 15/50; B05B 15/52;
(Continued)

(56) References Cited

U.S. PATENT DOCUMENTS

| 2,112,160 A * | 3/1938 | Johnson ............... A61M 31/00 604/518 |
| 3,581,940 A * | 6/1971 | Celia .................. B65D 81/3283 222/94 |

(Continued)

FOREIGN PATENT DOCUMENTS

WO   WO 03039375 A2   5/2003

OTHER PUBLICATIONS

International Search Report dated Jul. 11, 2018 in corresponding PCT Application No. PCT/US2018/028109; 5 Pages.
(Continued)

*Primary Examiner* — William R Carpenter
(74) *Attorney, Agent, or Firm* — K&L Gates LLP

(57) ABSTRACT

An assembly for mixing and dispensing a multi-component fluid includes a sheath having first and second fluid chambers, a chamber coupler, and a flexible tip. The chamber coupler forms first and second fluid channels. Additionally, the flexible tip forms a mixing chamber with a variable mixing volume and an outlet. The flexible tip is coupled to the chamber coupler near a distal end of the sheath. In the presence of an activation force, the flexible tip is forced out of the sheath and positioned in a dispensing state with a maximum mixing volume. In the absence of the activation force, the flexible tip is housed within the sheath and positioned in a non-dispensing state with a minimum mixing volume such that the outlet is substantially closed.

20 Claims, 6 Drawing Sheets

(58) Field of Classification Search
CPC .............. B05B 15/522; B05B 15/5223; B05B 15/5225; B05B 15/528; A61M 5/19; A61M 2005/3103; A61M 2005/3128; A61M 5/2066
See application file for complete search history.

(56) References Cited

U.S. PATENT DOCUMENTS

| | | | | | |
|---|---|---|---|---|---|
| 4,040,420 | A | * | 8/1977 | Speer | A61M 5/19 604/82 |
| 4,109,653 | A | * | 8/1978 | Kozam | A61M 5/19 604/191 |
| 5,497,946 | A | * | 3/1996 | Laidler | B05B 15/525 239/452 |
| 6,974,053 | B2 | * | 12/2005 | Lautre | B65D 47/2081 222/92 |
| 10,144,017 | B2 | * | 12/2018 | Davis | B01F 35/7164 |
| 2010/0096481 | A1 | * | 4/2010 | Hull | B05B 7/10 239/600 |
| 2011/0079300 | A1 | * | 4/2011 | Kneer | B65D 47/18 137/511 |
| 2015/0128873 | A1 | | 5/2015 | Prescott et al. | |
| 2018/0099295 | A1 | * | 4/2018 | Armbruster | B05B 1/323 |

OTHER PUBLICATIONS

Written Opinion of the International Searching Authority dated Jul. 11, 2018 in corresponding PCT Application No. PCT/US2018/028109; 6 Pages.
International Preliminary Report on Patentability Chapter II dated Jun. 18, 2019 in corresponding PCT Application No. PCT/US2018/028109; 11 Pages.

* cited by examiner

NON-CLOGGING DISPENSING DEVICE

CROSS-REFERENCE TO RELATED APPLICATIONS

The present application is a National Stage of International Application No. PCT/US2018/02819, filed on Apr. 18, 2016, which claims priority to U.S. Provisional Patent Application No. 62/487,261, filed on April 19, "NON-CLOGGING DISPENSING DEVICE", which application is incorporated herein by reference in its entirety.

BACKGROUND

Multi-component dispensing devices are used to mix and dispense multi-component fluids, such as sealants that need to be kept separated prior to dispensing. For example, several fluid constituents may be mixed together to form a biological sealant or adhesive. Sealants and adhesives are made by mixing each fluid component together, which react with each other to harden or set after they are mixed. Often times, the two fluid components react quickly and harden into the sealant or adhesive, such as a tissue adhesive. Because of the rapid reactivity following component contact, mixing the fluid components occurs only when the multi-component fluid is ready to be dispensed and applied.

In order for the sealant or adhesive to properly form, each fluid component should be well mixed before applying the multi-component fluid. Unfortunately, existing methods for dispensing multi-component biological sealants are often inadequate. For example, partially mixed fluid components may result in a sealant that does not sufficiently harden. If the multi-component fluid hardens in the tip, the tip clogs and prevents flow, typically requiring replacement of the tip. Furthermore, ejecting hardened components or obstructions may pose a hazard for a patient. For example, an ejected obstruction may cause trauma to tissue or organs and may also cause an embolism within a vessel.

Many current systems and methods for dispensing multi-component biological sealants rely solely on elastomeric properties of a flexible diaphragm to prevent clogging; these material properties are difficult to control and degrade over time. Additionally, under high pressure, the diaphragm may burst or rupture causing a clinical hazard or a further degradation of performance.

SUMMARY

The present disclosure provides improved non-clogging and self-cleaning dispensing applicators, systems, and methods. In one example embodiment, a self-cleaning applicator for mixing and dispensing a multi-component fluid includes a first fluid chamber and a second fluid chamber, a sheath, a chamber coupler, a flexible tip, a spring, and a grip. The sheath encloses the first and second fluid chambers, and the sheath has a restriction member at its distal end and a handgrip at its proximal end. The chamber coupler forms first fluid and second fluid channels, and the flexible tip forms a mixing chamber with a mixing volume and an outlet. Additionally, the flexible tip is coupled to the chamber coupler near the distal end of the sheath. The spring is positioned between the distal end of the sheath and the chamber coupler. The grip is connected to first and second plungers. The first and second fluid channels extend from the first and second fluid chambers respectively to the mixing chamber. Upon applying a force to the grip and an opposing force to the handgrip, the flexible tip is forced out of the restriction member and positioned in a dispensing state thereby increasing the mixing volume and allowing the multi-component fluid to exit the outlet. Additionally, removal of the application of the force and opposing force causes the restriction member to extend over the flexible tip and deform the flexible tip such that the mixing volume is reduced and the outlet is substantially closed in a non-dispensing state.

In another example embodiment, the mixing volume is variable, and the mixing volume changes from an active state to an inactive state through the expansion and compression of side walls of the flexible tip.

In one embodiment, the mixing volume and the cross-sectional area of second ends of the first and second fluid channels are minimized when the applicator is not dispensing the multi-component fluid.

In a further embodiment, minimizing the volume of the mixing chamber cleans the mixing chamber of the flexible tip. Preferably, the restriction member deforms the flexible tip and pushes sidewalls of the flexible tip in towards each other thereby providing a cleaning force to remove the remaining multi-component fluid from the flexible tip before the outlet closes.

In other example embodiments, the flexible tip is configured to transition from the dispensing state and the non-dispensing state multiple times such that multi-component fluids are dispensed through the outlet, cleaned from the flexible tip, and again dispensed through the outlet.

In a further embodiment, the first fluid channel and the second fluid channel includes a resiliently flexible pathway having walls that can be substantially closed to prevent flow of fluid to the mixing chamber.

In a further embodiment, the flexible tip is configured and dimensioned to substantially occupy the mixing volume when the restriction member is extended over the flexible tip.

In an example embodiment, the flexible tip closing in forces substantially all of the multi-component fluid components remaining in the mixing chamber out through the outlet.

In another example embodiment, the flexible tip is configured to expand at least one of radially and distally such that the flexible tip changes from the non-dispensing state to the dispensing state.

In a further embodiment, the flexible tip comprises a material that permits at least one of flexion and expansion.

In another example embodiment, at least a portion of the flexible tip comprises silicone.

In one embodiment, the spring is a coiled spring, a leaf spring, or an elastomeric material.

In an example embodiment, the chamber coupler and flexible tip are configured to slide from a first position to a second position upon compression of the spring.

In a second example embodiment, an assembly for mixing and dispensing a multi-component fluid includes a sheath having first and second fluid chambers, a chamber coupler, and a flexible tip. The chamber coupler forms first and second fluid channels. Additionally, the flexible tip forms a mixing chamber with a variable mixing volume and an outlet. The flexible tip is coupled to the chamber coupler near a distal end of the sheath. In the presence of an activation force, the flexible tip is forced out of the sheath and positioned in a dispensing state with a maximum mixing volume. In the absence of the activation force, the flexible tip is housed within the sheath and positioned in a non-dispensing state with a minimum mixing volume such that the outlet is substantially closed.

In one embodiment, the variable mixing volume changes from an active state to an inactive state through the expansion and compression of sidewalls of the flexible tip.

In another embodiment, transitioning between the maximum mixing volume and minimum mixing volume cleans the mixing chamber of the flexible tip. Preferably, the sheath deforms the flexible tip and pushes sidewalls of the flexible tip in towards each other, which provides a cleaning force to remove the remaining multi-component fluid from the flexible tip before the outlet closes.

In an example embodiment, the flexible tip is configured to transition from the dispensing state and the non-dispensing state multiple times such that multi-component fluids are dispensed through the outlet, cleaned from the flexible tip, and again dispensed through the outlet.

In a further embodiment, the flexible tip is configured and dimensioned to substantially occupy the variable mixing volume when the flexible tip is housed within the sheath.

In yet another embodiment, the flexible tip is configured to expand at least one of radially and distally such that the flexible tip changes from the non-dispensing state to the dispensing state.

In a further embodiment, the flexible tip comprises a material that permits at least one of flexion and expansion, preferably, silicone.

It is accordingly an advantage of the present disclosure to provide a non-clogging dispensing tip in a fluid delivery device.

It is another advantage of the present disclosure to provide a self-cleaning effect.

It is further advantage of the present disclosure to provide a dispensing device that may be used for multiple dispensing cycles that automatically self cleans without further input from a user.

Additional features and advantages of the disclosed welding apparatus and seal die are described in, and will be apparent from, the following Detailed Description and the Figures. The features and advantages described herein are not all-inclusive and, in particular, many additional features and advantages will be apparent to one of ordinary skill in the art in view of the figures and description. Also, any particular embodiment does not have to have all of the advantages listed herein. Moreover, it should be noted that the language used in the specification has been principally selected for readability and instructional purposes, and not to limit the scope of the inventive subject matter.

DETAILED DESCRIPTION OF EXAMPLE EMBODIMENTS

As discussed above, multi-component dispensing applicators, systems, and methods provide an improved dispensing device that prevents clogging and automatically self-cleans between uses. Clogging and obstructions, such as hardened residual adhesive in the tip, are problematic as they may cause injury to a patient if ejected and may increase costs associated with dispensing applicators as a clogged device may be inoperable or may require a new dispensing tip. Additionally, ejecting an obstruction may result in injury, such as trauma to tissues or organs and embolism within a vessel. The multi-component dispensing applicator discussed herein improves multi-component fluid dispensing by preventing clogging and performing an automatic self-cleaning operation between uses.

Figure 1A:
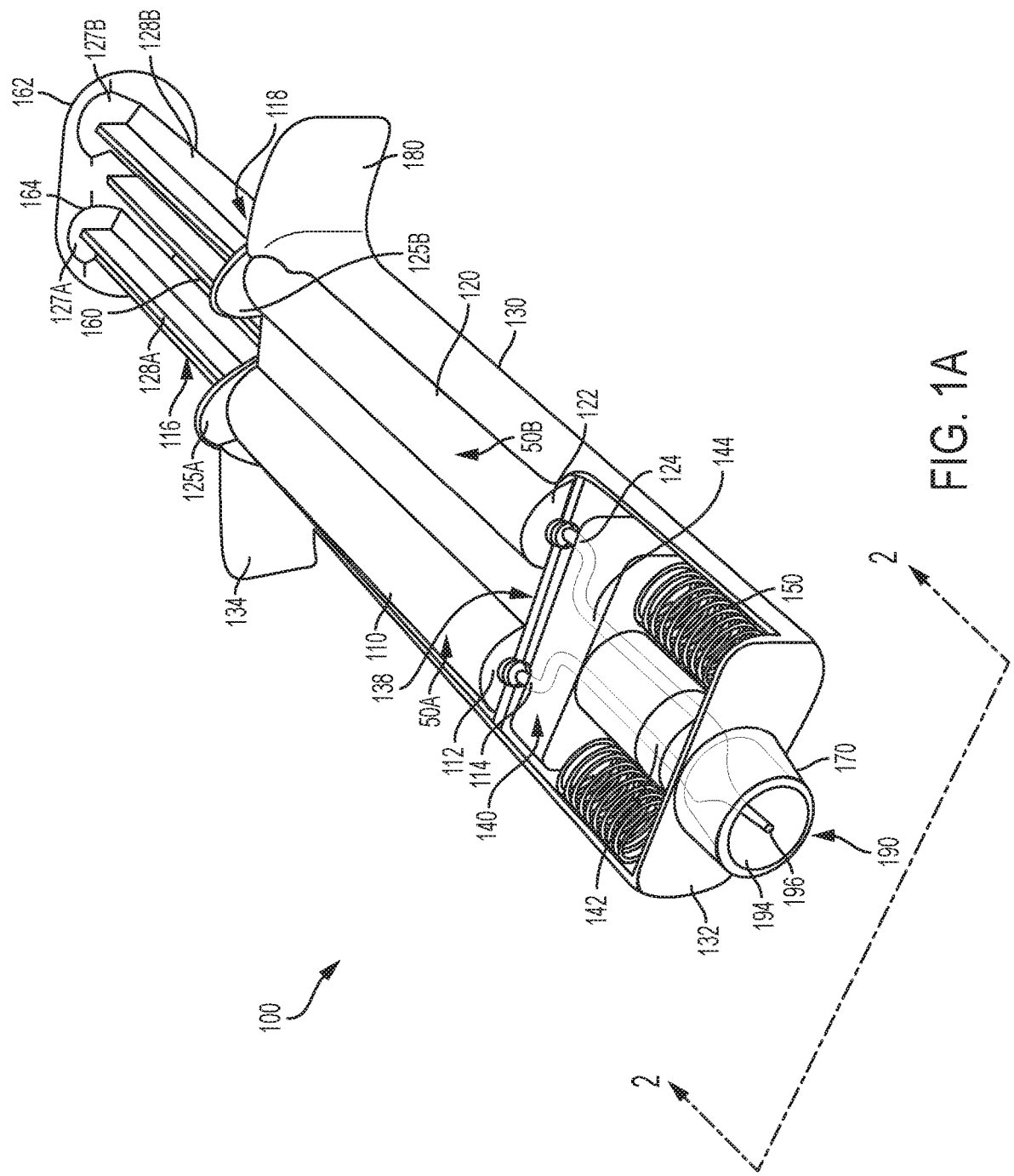
FIG. 1A is a schematic view of a self-cleaning applicator in a non-dispensing state according to an example embodiment of the present disclosure.
Figure 1B:
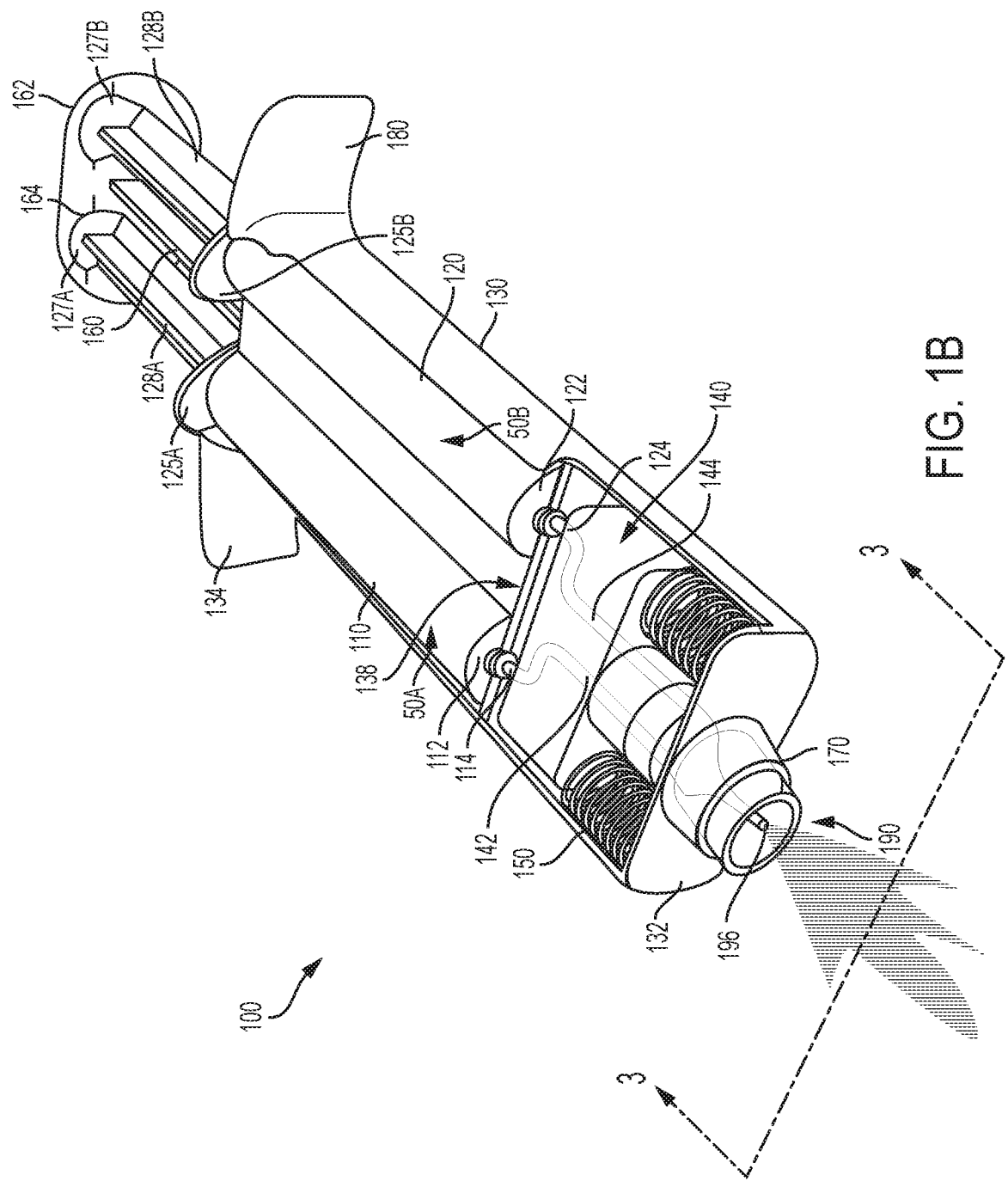
FIG. 1B is a schematic view of a self-cleaning applicator in a dispensing state according to an example embodiment of the present disclosure.

Referring to the drawings and in particular to FIGS. 1A and 1B, in one embodiment, a self-cleaning applicator 100 of the present disclosure is provided to mix and dispense multi-component fluids. In one embodiment, the self-cleaning applicator 100 includes a first fluid chamber 110, a second fluid chamber 120, a sheath 130 or body, a chamber coupler 140, a flexible tip 190, and one or more spring(s) 150. Sheath 130 encloses the first and second fluid chambers 110, 120. Additionally, sheath 130 may include a restriction member 170 at its distal end 132 and a handgrip 180 at its proximal end 134. In an example, sheath 130 may include guide rails that couple to the chamber coupler 140 and/or fluid chambers 110, 120 (e.g., syringes). As further detailed below, the sheath 130 is adapted to move axially when force is applied to the handgrip 180. It should be appreciated that sheath 130, restriction member 170, and handgrip 180 may be component parts that can be assembled together. Additionally, sheath 130 may be molded as a single piece that includes restriction member 170 and handgrip 180. Further, components may be bonded together via chemical fasteners. Chemical fasteners may include, for example, adhesives, chemical bonds, weld bonds or moldings suitable for securing components.

Additionally, the self-cleaning applicator may include a grip 162 and an activation rod 160. For example, the activation rod 160 may provide stability for grip 162. As discussed in more detail below, syringe plunger thumb flanges 127A-B may serve as grip 162. Additionally, grip 162 may be attached to syringe plungers. In addition to providing a gripping surface, grip 162 may link the syringe plungers 128A-B together to ensure that they move in tandem and dispense proper proportions of fluid from the first and second fluid chambers 110, 120.

Each fluid chamber (e.g., first fluid chamber 110 and second fluid chamber 120) may contain a reactive fluid. For example, the first fluid chamber 110 may include a first fluid 50A, and the second fluid chamber 120 may include a second fluid 50B. Fluids 50A-B may react to create a sealant or adhesive, such as a biological tissue sealant. Due to the reactivity of fluids 50A-B, they are separately stored in fluid chambers 110, 120. Particularly reactive multi-component fluids have a tendency to form clots within the fluid path of a dispensing device or applicator 100. For example, for reactive solutions such as biological tissue sealants, the dwell time to clot formation can be short, and in many cases just seconds. Therefore, it is advantageous to purge any excess reactive (i.e., mixed) solution from the nozzle or flexible tip 190 and fluid channels 142, 144 (discussed in more detail below) between uses.

As illustrated in FIG. 1A, the applicator 100 is in a non-dispensing state. Conversely, as illustrated in FIG. 1B, the applicator 100 is in a dispensing state. As the applicator 100 transitions between the dispensing state (FIG. 1B) and the non-dispensing state (FIG. 1A), the flexible tip 190 is advantageously and automatically cleaned of any residual material such that the applicator 100 does not clog between dispensing cycles. For example, each time the applicator 100 transitions from the dispensing state to the non-dispensing state, material is ejected from the flexible tip 190 outlet. As the flexible tip 190 is pulled into and deformed by the restriction member 170 the flexible tip 190 continues to deform until the outlet is closed, which advantageously prevents clogging and enables repeated use of applicator 100.

As illustrated in FIGS. 1A and 1B, first and second fluid chambers 110, 120 may be removable components, such as a syringe (e.g., hypodermic syringe). In an example embodiment, the first and second fluid chambers 110, 120 may be an integral part of the self-cleaning applicator 100 (as explained in more detail below). For example, the first fluid chamber 110 may include a dispensing end 112 with an opening 114 and an open end 116. Similarly, the second fluid chamber 120 may include a dispensing end 122 with an opening 124 and an open end 126. The dispensing ends 112, 122 may include a connector that is adapted to couple to each fluid channel 142, 144 in the chamber coupler 140 (discussed in more detail below). The connector may be a threaded connector, press-fit connector, or any other suitable connector that creates a sealed connection between the fluid chambers 110, 120 and fluid channels 142, 144. For example, the self-cleaning applicator 100 may accept standard Luer connectors (threaded or non-threaded). Additionally, the connector may provide additional safety by preventing installation of the wrong size or type of syringe. In an example, dispensing ends 112, 122 of fluid chambers 110, 120 may be detachably locked to the chamber coupler 140. Additionally, self-cleaning applicator may include plungers 128A-B that are adapted to push fluid through each fluid chamber (e.g., first and second fluid chambers 110, 120). Plunger 128A-B may extend along each fluid chamber 110, 120 and each plunger includes a plunger head that snugly engages sidewalls of the respective fluid chamber 110, 120. Each plunger 128A-B may also include a thumb flange 127A-B, hereinafter thumb flange(s) 127, at one end that extends beyond the open ends 116, 126 of the fluid chambers 110, 120.

The thumb flanges 127 may be coupled to the activation rod 160 and/or grip 162. For example, the activation rod 160 and/or grip 162 may include slots or recesses 164 that are formed within the activation rod 160 and/or grip 162 and configured to receive the thumb flanges 127 of the plungers 128A-B, hereinafter plunger(s) 128. The plungers 128 may be coupled to the activation rod 160 and/or grip 162 such that the plungers 128 move in unison with the activation rod 160. Additionally, the plungers 128 may be integrally formed with the activation rod 160 and/or grip 162. For example, the plungers 128 and the activation rod 160 may be a single piece. Additionally, the plungers 128 and grip 162 may be a single piece. Similarly, if removable syringes are used as fluid chambers 110, 120, finger flanges 125A-B of each syringe may assist with locking the syringes into sheath 130. In an example, the plungers 128 and activation rod 160 and/or grip 162 may be component pieces that are assembled together. As the activation rod 160 and plungers 128 are advanced through fluid chambers 110, 120 (e.g., by a user engaging and applying a force to grip 162), fluid is pushed through each fluid chamber 110, 120 towards the dispensing ends 112, 122 and out through openings 122, 124.

As discussed above, Sheath 130 may enclose the first and second fluid chambers 110, 120. As illustrated in FIGS. 1A and 1B, sheath 130 may partially enclose the first and second fluid chambers 110, 120 (e.g., removable syringes). For example, fluid chambers 110, 120 may be pressed into (e.g., clipped into) sheath 130. For example, sheath 130 may include openings or cavities that are adapted to accept syringes while still enabling the sheath 130 to move independent of the fluid chambers (e.g., syringes). Additionally, fluid chambers 110, 120 may be slid into sheath 130 from the proximal end 134 of sheath 130. In another example, sheath 130 may be a two-part component. For example, sheath 130 may include a sliding component attached to the handgrip 180 and restriction member 180, and a stationary component that includes two reservoirs that form fluid chambers 110, 120 and thus fully enclose such chambers. Additionally, the stationary component may include a wall 138 with openings that provides an interface between chamber coupler 140 and fluid channel openings 114, 124. For example, as described above, fluid chambers 110, 120, such as syringes, may clip into the stationary component of sheath 130. As illustrated in FIG. 1A and FIG. 1B, sheath 130 may also include a handgrip 180 at its proximal end. In another example, the sheath 130 may be configured and arranged such that thumb flange(s) 127 of the removable syringes used as fluid chambers 110, 120 can be used as the handgrip 180. As discussed in more detail below, handgrip 180 may be used to apply a force to sheath 130 when a force in an opposite direction is applied to grip 162.

Figure 2A:
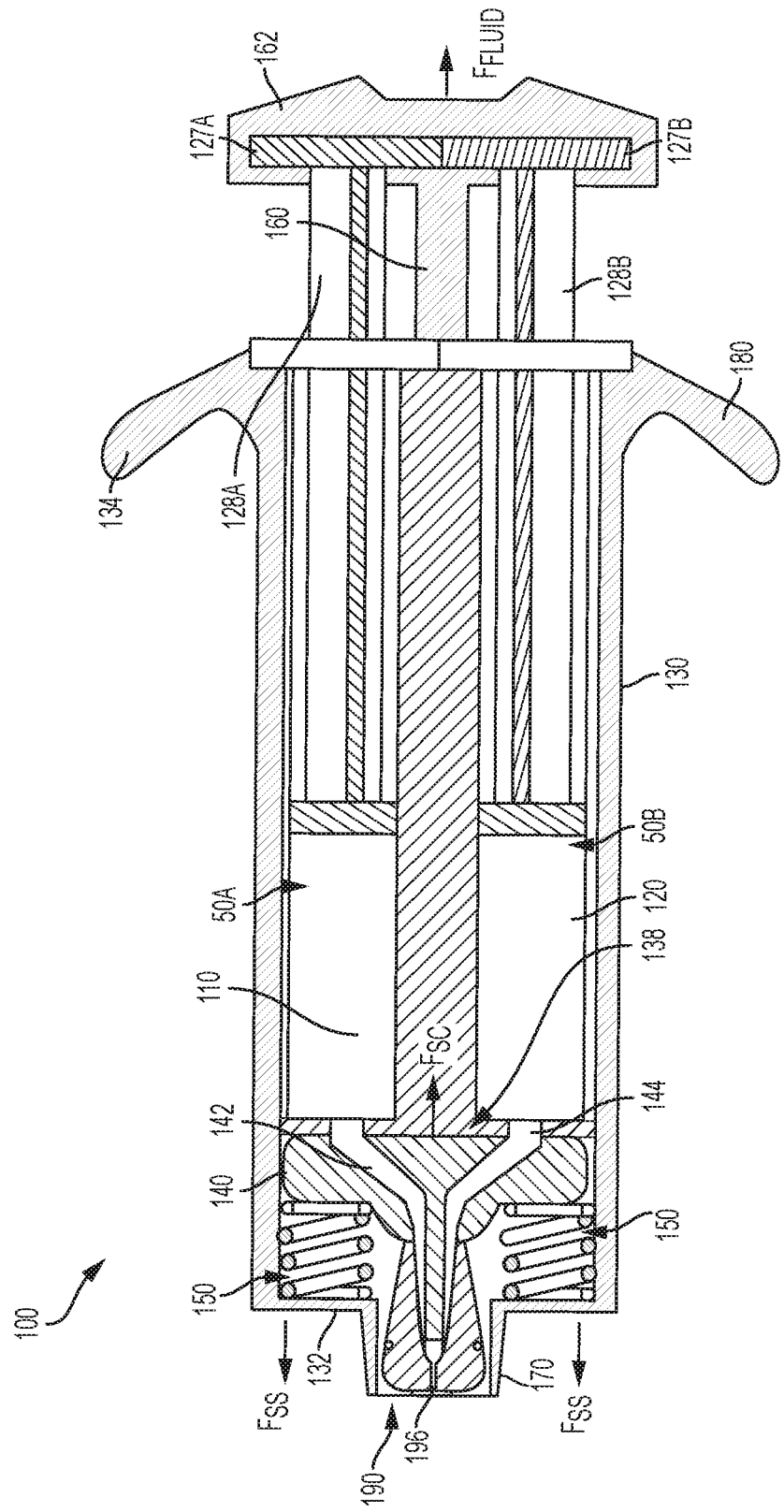
FIG. 2A is a cross-sectional view taken along line II-II of FIG. 1A of a self-cleaning applicator in a non-dispensing state according to an example embodiment of the present disclosure.
Figure 2B:
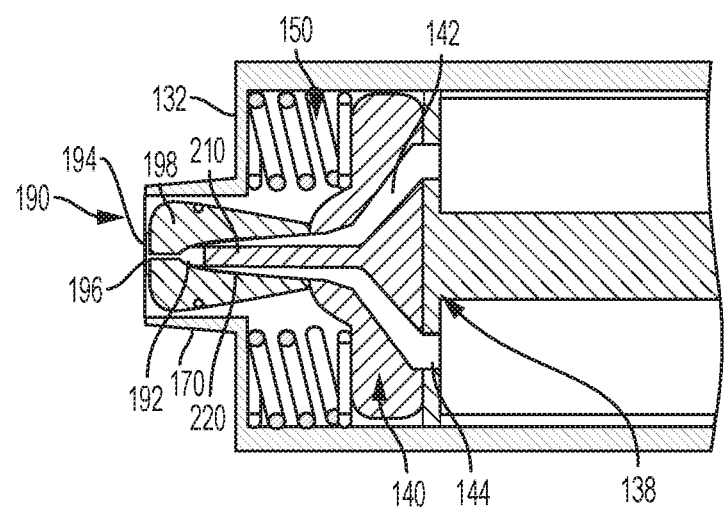
FIG. 2B is an enlarged detail view of the self-cleaning application in FIG. 2A.

Additionally, chamber coupler 140 may form first and second fluid channels 142, 144. For example, the chamber coupler 140 may include a first fluid channel 142 or fluid passage that extends from the first fluid chamber 110 to a mixing chamber 192 (discussed in more detail below) within flexible tip 190. Additionally, chamber coupler 140 may include a second fluid channel 144 or fluid passage that extends from the second fluid chamber 120 to the mixing chamber 192 within flexible tip 190. Fluid channels 142, 144 may form a "Y" configuration (as illustrated in FIGS. 2A and 2B) or "T" configuration (as illustrated in FIGS. 1A and 1B), that extends from the fluid channel openings 114, 124 of fluid chambers 110, 120 to the mixing chamber 192. Additionally, fluid channels 142, 144 may have any other suitable arrangement that enables fluid communication between fluid chambers 110, 120 and the mixing chamber 192. First and second fluid channels 142, 144 provide fluid communication between fluid chambers 110, 120 and mixing chamber 192. For example, fluid channels 142, 144 provide continuous fluid passages from fluid chambers 110, 120 through chamber coupler 140 to mixing chamber 192. While the self-cleaning applicator 100 and chamber coupler 140 are shown receiving two sources of fluid, it should be appreciated that applicator 100 and chamber coupler 140 may be configured to receive more than two sources of fluid. For example, applicator 100 may be configured to mix and dispense an adhesive or sealant, such as a biological sealant that is made up of three or more component fluids. It should be appreciated that the self-cleaning applicator 100 may include additional fluid chambers. For example, the applicator 100 illustrated in FIG. 1A and FIG. 1B shows two fluid chambers 110, 120, however, three or more fluid chambers may be used. For example, some multi-component fluids may include three or more fluids that are mixed to form a sealant or adhesive.

In an example, the chamber coupler 140 may be made of plastic, rubber, polymer, or any other suitable rigid or semi-rigid material. For example, chamber coupler 140 may be made of polycarbonate, polypropylene, polyethylene, acrylonitrile butadiene styrene (abs), a combination thereof, or the like. The chamber coupler 140 may be coupled to the flexible tip 190. For example, flexible tip 190 may be form fitted to the end of chamber coupler 140. Additionally, the flexible tip 190 may be affixed to the chamber coupler 140 by heat sealing. In another example, flexible tip 190 may be attached to chamber coupler 140 via a threaded fitting, snap-fit, adhesive, or any other suitable fastener such that the flexible tip 190 moves in conjunction with the chamber coupler 140. Additionally, flexible tip 190 may be removable or permanently attached to chamber coupler 140. For example, after a specified lifetime (e.g., 2 months) or after a specified number of uses (e.g., 50 uses), the flexible tip 190 may be replaced.

Figure 3A:
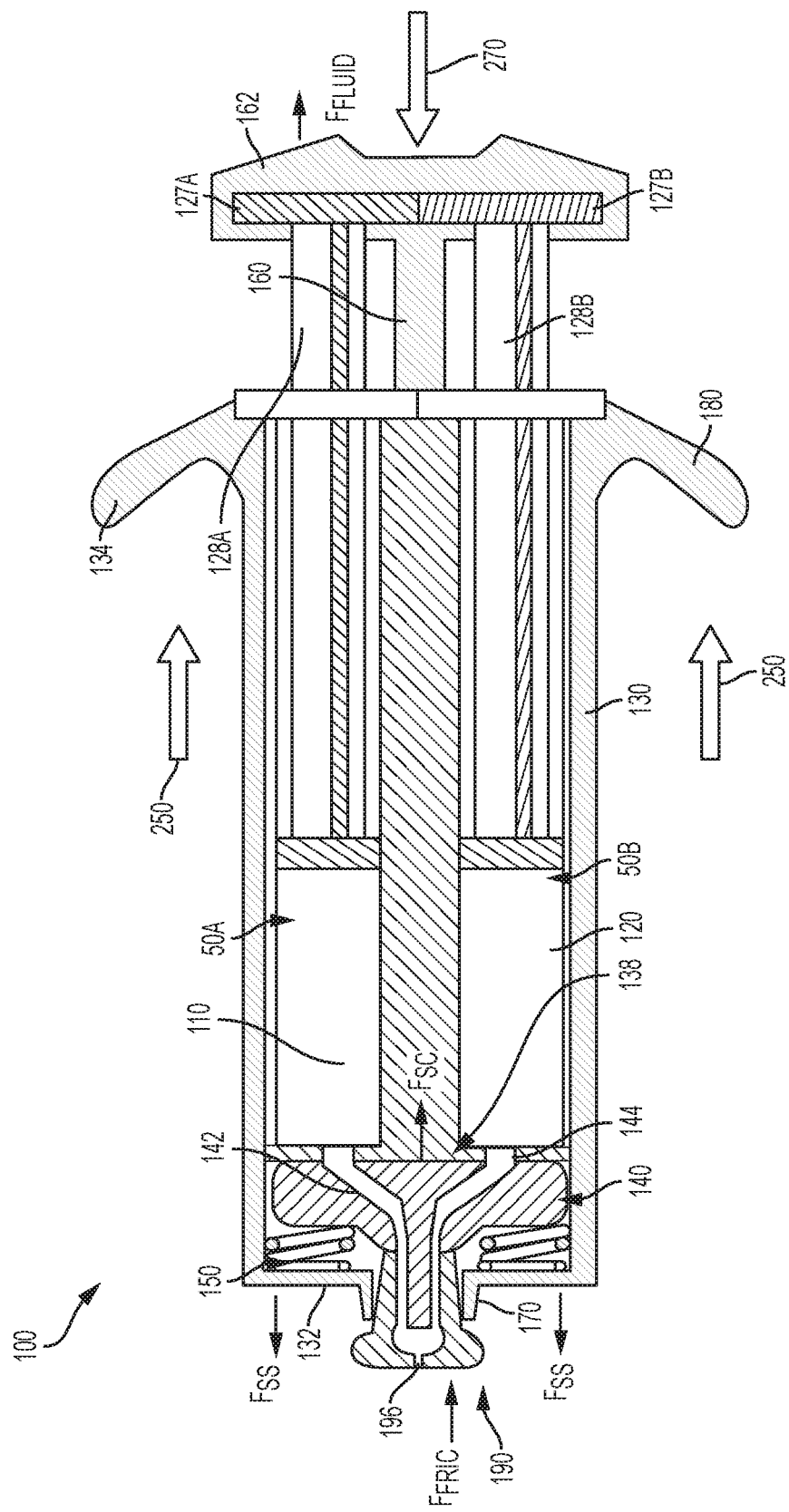
FIG. 3A is a cross-sectional view taken along line of FIG. 1B of a self-cleaning applicator in a dispensing state according to an example embodiment of the present disclosure.
Figure 3B:
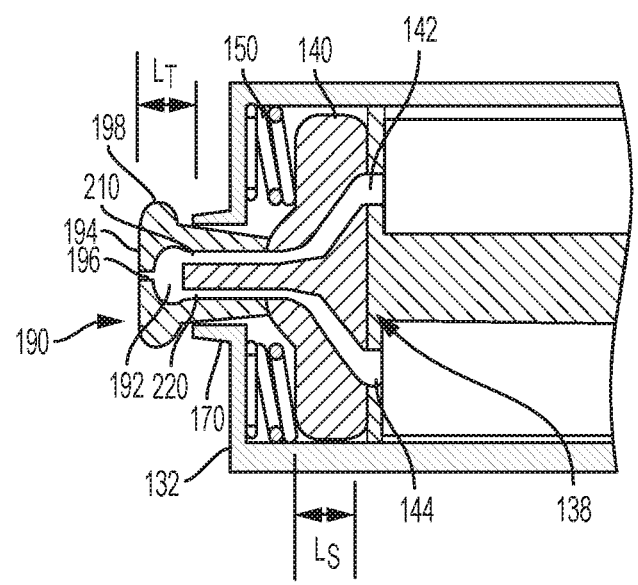
FIG. 3B is an enlarged detail view of the self-cleaning application in FIG. 3A.

FIG. 2A, which is a cross-sectional view taken along line II-II of FIG. 1A and further illustrated in FIG. 2B, which is cross-sectional view taken along line of FIG. 1B. As illustrated in FIGS. 3A and 3B, which are enlarged detail views of FIGS. 2A and 2B, flexible tip 190 defines a mixing chamber 192 between its dispensing face 194 and sidewalls 198. Mixing chamber 192 is where fluid components first come into contact and begin mixing before being dispensed as a multi-component fluid. In an example, flexible tip 190 may be a cylindrical with an open end connected to the chamber coupler 140 and the dispensing face 194 pointing away from the sheath 130. For example, flexible tip 190 may be made of silicone or another biocompatible material with proper elastomeric properties, such as polyisoprene, butyl rubber, or the like. Additionally, flexible tip 190 has an outlet 196 on its dispensing face 194 that is configured to eject the mixed fluid components. Outlet 196 is preferably located in the center of dispensing face 194 such that it is aligned with the center of mixing chamber 192 between first and second fluid channels 142, 144. The outlet 196 may be substantially circular. In another example embodiment, the outlet 196 may be a slit, such as a split septum. Various other outlet configurations and geometries may be used. As discussed in further detail below, in the dispensing state (FIGS. 3A and 3B), the flexible tip 190 may flex or expand under pressure thereby allowing the mixed fluid to exit outlet 196. Additionally, flexible tip 190 may have sufficient flexibility such that it collapses inward in the non-dispensing state (FIGS. 2A 2B). For example, flexible tip 190 may be made from silicon, rubber, or the like such that it can flex (e.g., expand or contract) as it enters and exits sheath 130.

As illustrated in FIGS. 1B and 3A, the flexible tip 190 may have a ridge or additional thickness of material near the dispensing face 194 to ensure that the flexible tip 190 fits tightly within the restriction member 170. Additionally, by having a shape as depicted in FIGS. 1B and 3A, the applicator 100 advantageously requires more than a nominal force to start dispensing fluid thereby reducing accidental applications and or over application of sealant. For example, the ridge near the dispensing face 194 may enhance the frictional fit within restriction member 170 of sheath 130. Additionally, the ridge may be shaped to ensure that the mixing volume 192 is substantially reduced to zero and the first and second fluid channels 142, 144 are substantially closed as the applicator 100 transitions to the non-dispensing state.

As illustrated in FIGS. 2A and 2B, in the non-dispensing state, flexible tip 190 is compressed within restriction member 170. In the non-dispensing state, there is insufficient force applied to the handgrip 180 or the grip 162 to overcome the opposite force applied by springs 150. As discussed above, grip 162 may be coupled to syringe plungers 128. In another example, grip 162 may include an activation rod 160 for added stability. For example, in the non-dispensing state, springs 150 are partially compressed and apply a force ($F_{SS}$) to sheath 130 that pushes sheath 130 over flexible tip 190. Additionally, in the non-dispensing state, springs 150 apply a force ($F_{SC}$) to chamber coupler 140, which may be coupled to flexible tip 190. In the non-dispensing state, springs 150 are in a partially compressed state, thereby causing the chamber coupler 140 to hold the flexible tip 190 within the restriction member 170 because the spring forces ($F_{SS}$) and ($F_{SC}$) urge the sheath in one direction and the coupled components (e.g., flexible tip 190 and chamber coupler 140) in an opposite direction. In the non-dispensing state, the restriction member causes the flexible tip 190 to deform and decrease the mixing volume of the mixing chamber 192. For example, the restriction member 170 is shaped such that the sidewalls 198 of flexible tip 190 compress and collapse inward to substantially reduce the mixing volume to zero.

As shown in FIG. 2B, as the mixing volume is reduced, the fluid outlet ends 210, 220 of fluid channels 114, 124 are also closed. For example, the cross-sectional area of the outlet ends 210, 220 of the first and second fluid channels 114, 124 are substantially minimized when the applicator 100 is in the non-dispensing state. The fluid channels 114, 124 may close due to the compressive nature of the material used for chamber coupler 140. In another embodiment, the flexible tip may deform to block the second ends of the first and second fluid channels 114, 124 such that they are substantially blocked and the fluid communication between the fluid chambers 110, 120 and the mixing chamber 192 is interrupted.

As illustrated in FIGS. 3A and 3B, in the dispensing state, a user may apply force 250 to the handgrip 180, which simultaneously applies an opposite force 270 to the grip 162, which may include an activation rod 160. It should be appreciated that the forces 250, 270 need only have some component force in opposite directions such that the handgrip 180 is pulled towards the grip 162 on the activation rod 160 (e.g., the handgrip 180 and grip 162 move closer together). The application of force(s) 250, 270 must be sufficient to overcome the spring forces ($F_{SS}$) and ($F_{SC}$), friction force ($F_{FRIC}$) exerted by the flexible tip 190 within restriction member 170, and fluid forces ($F_{FLUID}$) to transition the applicator 100 in a dispensing state. For example, if forces 250 and 270 are sufficient to further compresses springs 150, the sheath 130 is pulled in an opposite direction of the chamber coupler 140 (e.g., by a length that the springs compress $L_S$) due to the force applied to the handgrip 180.

As the springs 150 further compress due to forces 250, 270, the chamber coupler 140 extends towards the distal end 132 of the sheath 130 as the sheath 130 moves relative to the chamber coupler 140 and flexible tip 190. For example, force 250 applied to handgrip 180 is transferred through sheath 130 which engages the bottom end of spring 150 (e.g., surface of spring closest to distal end 132 of sheath 130). Wall 138 of the stationary component of sheath 130 provides a backstop that holds the chamber coupler 140 stationary relative to the sheath 130 such that a force is applied to the top end of spring(s) 150 (e.g., surface of spring closest to proximal end 134 of sheath 130). Additionally, force 270 applied to grip 162 and optionally activation rod 160 is transferred through the grip 162 to the syringe plungers 128 and to the fluid components within the fluid chambers 110, 120. While the sheath 130 retracts, the flexible tip 190 extends past the sheath 130 and returns to its natural, uncompressed state. For example, as the springs 150 compress by a length ($L_S$), the flexible tip 190 extends out of restriction member 170 by a length ($L_T$).

When flexible tip 190 is in the uncompressed state, the mixing volume of the mixing chamber 192 increases, thereby allowing component fluids to flow through the fluid channels 142, 144 and mix within the mixing chamber 192. Further application of force 270 to the grip 162, and thereby the plungers 128, pushes fluid through fluid chambers 110, 120 and fluid channels 142, 144 where it mixes in mixing chamber 192. As more fluid enters mixing chamber 192, the mixed fluid is pushed from the mixing chamber 192 through the outlet 196 of flexible tip 190. As discussed above, the flexible nature of the tip 190 allows the flexible tip 190 to expand to its uncompressed state upon exiting the sheath 130. For example, upon exiting the sheath 130, the flexible tip 190 may expand and/or flex radially outwardly. Such expansion may cause the outlet 196 to increase in size and/or open. For example, the diameter of the outlet 196 may enlarge or the split septum may slightly open.

As the flexible tip 190 returns to its natural, uncompressed state, fluid communication between the fluid chambers 110, 120 and mixing chamber 192 is restored. For example, as the flexible tip 190 expands, the chamber coupler 140 may return to its original shape and the fluid channels 142, 144 may enable fluid components to enter the mixing chamber 192. In an example, applicator 100 may remain in the dispensing state as long as sufficient force is applied against the activation rod 160 and handgrip 180. In the absence of sufficient force from a user, the applicator 100 may return to the non-dispensing state in which there is substantially no liquid component in mixing chamber 192.

The self-cleaning feature described above advantageously occurs automatically after each dispensing cycle once a user stops applying force to the applicator 100. For example, as forces 250, 270 are reduced or no longer applied such that they are insufficient to overcome the spring forces ($F_{SS}$) and ($F_{SC}$) applied by the springs 150 to the sheath 130 and chamber coupler 140, the springs 150 expand until the system is in equilibrium. As the springs 150 expand, the spring forces urge the sheath 130 over the flexible tip 190. It should be appreciated that as the sheath 130 extends over the flexible tip 190, the spring force needs to be sufficiently strong to overcome a friction force caused by the flexible tip 190 interacting with walls of restriction member 170. Therefore, springs 150 must have a suitable spring coefficient that enables applicator 100 to automatically transition from a dispensing state to a non-dispensing state. By self-cleaning after each dispensing cycle, the applicator 100 advantageously prevents clogging by removing residual fluid in the mixing chamber 192 and sealing the outlet 196 and fluid channels 142, 144 thereby preventing additional fluid from fluid chambers 110, 120 from entering the mixing chamber 192 until the device is ready to dispense again. For example, as the flexible tip 190 starts deforming as it is pulled into sheath restriction member 170, fluid channels 142, 144 are closed and the remaining mixed fluid is dispensed as the mixing volume continually decreases. The mixing volume continues to decrease and the mixed fluid is dispensed from outlet 196 of flexible tip 190 until the mixing volume is substantially zero and all of the mixed fluid has dispensed. When the sheath 130 fully extends over flexible tip 190 and the flexible tip 190 is fully compressed and/or deformed, the outlet 196 may also close to prevent any external contamination to mixing chamber 192.

Aspects of the subject matter described herein may be useful alone or in combination with one or more other aspects described herein. In a 1st exemplary aspect of the present disclosure, a self-cleaning applicator for mixing and dispensing a multi-component fluid includes a sheath and a flexible tip. The sheath has a proximal end and a distal end. Additionally, the sheath partially encloses the at least two fluid chambers. The flexible tip forms a mixing chamber in fluid communication with the at least two chambers.

In accordance with a 2nd exemplary aspect of the present disclosure, which may be used in combination with any one or more of the preceding aspects (e.g., the 1st aspect), the sheath includes a restriction member at the distal end and a handgrip at the proximal end.

In accordance with a 3rd exemplary aspect of the present disclosure, which may be used in combination with any one or more of the preceding aspects (e.g., the 1st or 2nd aspect), the applicator further includes a chamber coupler forming a first fluid channel and a second fluid channel.

In accordance with a 4th exemplary aspect of the present disclosure, which may be used in combination with any one or more of the preceding aspects (e.g., the 3rd aspect), the flexible tip forms a mixing chamber with a mixing volume and an outlet, the flexible tip coupled to the chamber coupler near the distal end of the sheath.

In accordance with a 5th exemplary aspect of the present disclosure, which may be used in combination with any one or more of the preceding aspects (e.g., the 4th aspect), the applicator further includes an activation rod that has a grip connected to a first plunger, a second plunger, and the chamber coupler. The first fluid channel extends from the first fluid chamber to the mixing chamber and the second fluid channel extends from the second fluid chamber to the mixing chamber. Upon applying a force to the activation rod and an opposing force to the sheath, the flexible tip is forced out of the sheath and positioned in a dispensing state thereby increasing the mixing volume and allowing the multi-component fluid to exit the outlet. Removal of the application of the force and opposing force causes the sheath to extend over the flexible tip and deform the flexible tip such that the mixing volume is reduced and the outlet is substantially closed in a non-dispensing state.

In accordance with a 6th exemplary aspect of the present disclosure, which may be used in combination with any one or more of the preceding aspects (e.g., the 3rd to 5th aspect), the applicator further includes a spring positioned between the distal end of the sheath and the chamber coupler.

In accordance with a 7th exemplary aspect of the present disclosure, which may be used in combination with any one or more of the preceding aspects (e.g., the 6th aspect), the spring is a coiled spring, a leaf spring, or an elastomeric material.

In accordance with an 8th exemplary aspect of the present disclosure, which may be used in combination with any one or more of the preceding aspects (e.g., the 5th to 7th aspect), the mixing volume is variable and the mixing volume changes from an active state to an inactive state through the expansion and compression of side walls of the flexible tip.

In accordance with a 9th exemplary aspect of the present disclosure, which may be used in combination with any one or more of the preceding aspects (e.g., the 8th aspect), the mixing volume and the cross-sectional area of second ends of the first and second fluid channels are minimized when the applicator is not dispensing the multi-component fluid.

In accordance with a 10th exemplary aspect of the present disclosure, which may be used in combination with any one or more of the preceding aspects (e.g., the 5th to 9th aspect), minimizing the volume of the mixing chamber cleans the mixing chamber of the flexible tip. Preferably, the sheath deforms the flexible tip and pushes side walls of the flexible tip in towards each other thereby providing a cleaning force to remove the remaining multi-component fluid from the flexible tip before the outlet closes.

In accordance with an 11th exemplary aspect of the present disclosure, which may be used in combination with any one or more of the preceding aspects (e.g., the 5th to 10th aspect), the flexible tip is configured to transition from the dispensing state and the non-dispensing state multiple times such that multi-component fluids are dispensed through the outlet, cleaned from the flexible tip, and again dispensed through the outlet.

In accordance with a 12th exemplary aspect of the present disclosure, which may be used in combination with any one or more of the preceding aspects (e.g., the 5th to 11th aspect), the first fluid channel and the second fluid channel comprises a resiliently flexible pathway having walls that can be substantially closed to prevent flow of fluid to the mixing chamber.

In accordance with a 13th exemplary aspect of the present disclosure, which may be used in combination with any one or more of the preceding aspects (e.g., the 5th to 12th aspect), the flexible tip is configured and dimensioned to substantially occupy the mixing volume when the sheath is extended over the flexible tip.

In accordance with a 14th exemplary aspect of the present disclosure, which may be used in combination with any one or more of the preceding aspects (e.g., the 5th to 13th aspect), the flexible tip closing in forces substantially all of the multi-component fluid components remaining in the mixing chamber out through the outlet.

In accordance with a 15th exemplary aspect of the present disclosure, which may be used in combination with any one or more of the preceding aspects (e.g., the 1st to 14th aspect), the flexible tip is configured to expand radially and/or distally such that the flexible tip changes from the non-dispensing state to the dispensing state.

In accordance with a 16th exemplary aspect of the present disclosure, which may be used in combination with any one or more of the preceding aspects (e.g., the 1st to 15th aspect), the flexible tip comprises a material that permits flexion and/or expansion.

In accordance with a 17th exemplary aspect of the present disclosure, which may be used in combination with any one or more of the preceding aspects (e.g., the 1st to 16th aspect), at least a portion of the flexible tip comprises silicone.

Aspects of the subject matter described herein may be useful alone or in combination with one or more other aspects described herein. In an 18th exemplary aspect of the present disclosure, an assembly for mixing and dispensing a multi-component fluid including a sheath, a chamber coupler, and a flexible tip. The sheath has first and second fluid chambers. The chamber coupler forms a first fluid channel and a second fluid channel. The flexible tip forms a mixing chamber with a variable mixing volume and an outlet. The flexible tip is coupled to the chamber coupler near a distal end of the sheath. In the presence of an activation force, the flexible tip is forced out of the sheath and positioned in a dispensing state with a maximum mixing volume. In the absence of the activation force, the flexible tip is housed within the sheath and positioned in a non-dispensing state with a minimum mixing volume such that the outlet is substantially closed.

In accordance with a 19th exemplary aspect of the present disclosure, which may be used in combination with any one or more of the preceding aspects (e.g., the 18th aspect), the variable mixing volume changes from an active state to an inactive state through the expansion and compression of side walls of the flexible tip.

In accordance with a 20th exemplary aspect of the present disclosure, which may be used in combination with any one or more of the preceding aspects (e.g., the 18th or 19th aspect), transitioning between the maximum mixing volume and minimum mixing volume cleans the mixing chamber of the flexible tip. Preferably, the sheath deforms the flexible tip and pushes side walls of the flexible tip in towards each other, which provides a cleaning force to remove the remaining multi-component fluid from the flexible tip before the outlet closes.

In accordance with a 21st exemplary aspect of the present disclosure, which may be used in combination with any one or more of the preceding aspects (e.g., the 18th to 20th aspect), the flexible tip is configured to transition from the dispensing state and the non-dispensing state multiple times such that multi-component fluids are dispensed through the outlet, cleaned from the flexible tip, and again dispensed through the outlet.

In accordance with a 22nd exemplary aspect of the present disclosure, which may be used in combination with any one or more of the preceding aspects (e.g., the 18th to 21st aspect), the flexible tip is configured and dimensioned to substantially occupy the variable mixing volume when the flexible tip is housed within the sheath.

In accordance with a 23rd exemplary aspect of the present disclosure, which may be used in combination with any one or more of the preceding aspects (e.g., the 18th to 22nd aspect), the flexible tip is configured to expand radially and/or distally such that the flexible tip changes from the non-dispensing state to the dispensing state.

In accordance with a 24th exemplary aspect of the present disclosure, which may be used in combination with any one or more of the preceding aspects (e.g., the 18th to 23rd aspect), the flexible tip comprises a material that permits flexion and/or expansion, preferably, silicone.

Aspects of the subject matter described herein may be useful alone or in combination with one or more other aspects described herein. In a 25th exemplary aspect of the present disclosure, a self-cleaning applicator for mixing and dispensing a multi-component fluid includes a first fluid chamber and a second fluid chamber, a sheath, a chamber coupler, a flexible tip, a spring, and a grip. The sheath encloses the first and second fluid chambers. Additionally, the sheath has a restriction member at a distal end and a handgrip at a proximal end. The chamber coupler forms a first fluid channel and a second fluid channel. The flexible tip forms a mixing chamber with a mixing volume and an outlet. Additionally, the flexible tip is coupled to the chamber coupler near the distal end of the sheath. The spring is positioned between the distal end of the sheath and the chamber coupler. The grip is connected to a first plunger and a second plunger. The first fluid channel extends from the first fluid chamber to the mixing chamber and the second fluid channel extends from the second fluid chamber to the mixing chamber. Upon applying a force to the grip and an opposing force to the handgrip, the flexible tip is forced out of the restriction member and positioned in a dispensing state thereby increasing the mixing volume and allowing the multi-component fluid to exit the outlet. Removal of the application of the force and opposing force causes the restriction member to extend over the flexible tip and deform the flexible tip such that the mixing volume is reduced and the outlet is substantially closed in a non-dispensing state.

In accordance with a 26th exemplary aspect of the present disclosure, which may be used in combination with any one or more of the preceding aspects (e.g., the 25th aspect), minimizing the volume of the mixing chamber cleans the mixing chamber of the flexible tip. Preferably, the restriction member deforms the flexible tip and pushes side walls of the flexible tip in towards each other thereby providing a cleaning force to remove the remaining multi-component fluid from the flexible tip before the outlet closes.

In accordance with a 27th exemplary aspect of the present disclosure, which may be used in combination with any one or more of the preceding aspects (e.g., the 25th or 26th aspect), the flexible tip is configured to transition from the dispensing state and the non-dispensing state multiple times such that multi-component fluids are dispensed through the outlet, cleaned from the flexible tip, and again dispensed through the outlet.

In accordance with a 28th exemplary aspect of the present disclosure, which may be used in combination with any one or more of the preceding aspects (e.g., the 25th to 27th aspect), the flexible tip is configured and dimensioned to substantially occupy the mixing volume when the restriction member is extended over the flexible tip.

In accordance with a 29th exemplary aspect of the present disclosure, which may be used in combination with any one or more of the preceding aspects (e.g., the 25th to 28th aspect), the spring is a coiled spring, a leaf spring, or an elastomeric material.

In accordance with a 30th exemplary aspect of the present disclosure, which may be used in combination with any one or more of the preceding aspects (e.g., the 25th to 29th aspect), the chamber coupler and flexible tip are configured to slide from a first position to a second position upon compression of the spring.

In accordance with a 31st exemplary aspect of the present disclosure, which may be used in combination with any one or more of the preceding aspects (e.g., the 25th to 30th aspect), the chamber coupler and flexible tip are configured to slide from a first position to a second position upon compression of the spring.

To the extent that any of these aspects are mutually exclusive, it should be understood that such mutual exclusivity shall not limit in any way the combination of such aspects with any other aspect whether or not such aspect is explicitly recited. Any of these aspects may be claimed, without limitation, as a system, method, apparatus, device, medium, etc.

The many features and advantages of the present disclosure are apparent from the written description, and thus, the appended claims are intended to cover all such features and advantages of the disclosure. Further, since numerous modifications and changes will readily occur to those skilled in the art, the present disclosure is not limited to the exact construction and operation as illustrated and described. Therefore, the described embodiments should be taken as illustrative and not restrictive, and the disclosure should not be limited to the details given herein but should be defined by the following claims and their full scope of equivalents, whether foreseeable or unforeseeable now or in the future.

The invention is claimed as follows:

1. An assembly for mixing and dispensing a multi-component fluid, the assembly comprising:

a sheath having first and second fluid chambers, a proximal end and a distal end, wherein the sheath includes a restriction member at the distal end and a handgrip at the proximal end;

a chamber coupler forming a first fluid channel and a second fluid channel; and a flexible tip forming a mixing chamber with a variable mixing volume and an outlet, the flexible tip coupled to the chamber coupler near the distal end of the sheath, wherein in the presence of an activation force, the flexible tip is forced out of the restriction member of the sheath and positioned in a dispensing state with a maximum mixing volume, and wherein in the absence of the activation force, the restriction member extends over the flexible tip and deforms the flexible tip as the flexible tip is housed within the sheath and positioned in a non-dispensing state with a minimum mixing volume such that the outlet is substantially closed.

2. The assembly of claim 1, wherein the variable mixing volume changes from an active state to an inactive state through the expansion and compression of side walls of the flexible tip.

3. The assembly of claim 1, wherein transitioning between the maximum mixing volume and minimum mixing volume cleans the mixing chamber of the flexible tip, wherein, the sheath deforms the flexible tip and pushes side walls of the flexible tip in towards each other which provides a cleaning force to remove the remaining multi-component fluid from the flexible tip before the outlet closes.

4. The assembly of claim 1, wherein the flexible tip is configured to transition from the dispensing state and the non-dispensing state multiple times such that multi-component fluids are dispensed through the outlet, cleaned from the flexible tip, and again dispensed through the outlet.

5. The assembly of claim 1, wherein the flexible tip is configured and dimensioned to substantially occupy the variable mixing volume when the flexible tip is housed within the sheath.

6. The assembly of claim 1, wherein the flexible tip is configured to expand at least one of radially and distally such that the flexible tip changes from the non-dispensing state to the dispensing state.

7. The assembly of claim 1, wherein the flexible tip comprises a material that permits at least one of flexion and expansion.

8. The assembly of claim 7, wherein the material is silicone.

9. The assembly of claim 1, further comprising an activation rod having a grip connected to a first plunger, a second plunger, and the chamber coupler, wherein
   the first fluid channel extends from the first fluid chamber to the mixing chamber;
   the second fluid channel extends from the second fluid chamber to the mixing chamber, and
   wherein upon applying a force to the activation rod and an opposing force to the sheath, the flexible tip is forced out of the sheath and positioned in the dispensing state, and wherein removal of the application of the force and opposing force causes the sheath to extend over the flexible tip and deform the flexible tip such that the mixing volume is reduced and the outlet is substantially closed in the non-dispensing state.

10. The assembly of claim 1, further comprising a spring positioned between the distal end of the sheath and the chamber coupler.

11. The assembly of claim 10, wherein the spring is one of a coiled spring, a leaf spring, and an elastomeric material.

12. The assembly of claim 1, wherein the flexible tip is configured and dimensioned to substantially occupy the mixing volume when the sheath is extended over the flexible tip.

13. The assembly of claim 1, wherein the flexible tip is configured to force substantially all of the multi-component fluid components remaining in the mixing chamber out through the outlet as the flexible tip transitions from the dispensing state to the non-dispensing state.

14. A self-cleaning applicator for mixing and dispensing a multi-component fluid, the applicator comprising:
- a first fluid chamber and a second fluid chamber;
- a sheath enclosing the first and second fluid chambers, the sheath having a restriction member at a distal end and a handgrip at a proximal end;
- a chamber coupler forming a first fluid channel and a second fluid channel;
- a flexible tip forming a mixing chamber with a mixing volume and an outlet, the flexible tip coupled to the chamber coupler near the distal end of the sheath;
- a spring positioned between the distal end of the sheath and the chamber coupler; and
- a grip connected to a first plunger and a second plunger, wherein
    - the first fluid channel extends from the first fluid chamber to the mixing chamber,
    - the second fluid channel extends from the second fluid chamber to the mixing chamber, and
    - wherein upon applying a force to the grip and an opposing force to the handgrip, the flexible tip is forced out of the restriction member and positioned in a dispensing state thereby increasing the mixing volume and allowing the multi-component fluid to exit the outlet, and wherein removal of the application of the force and opposing force causes the restriction member to extend over the flexible tip and deform the flexible tip such that the mixing volume is reduced and the outlet is substantially closed in a non-dispensing state.

15. The applicator of claim 14, wherein minimizing the volume of the mixing chamber cleans the mixing chamber of the flexible tip, wherein, the restriction member deforms the flexible tip and pushes side walls of the flexible tip in towards each other thereby providing a cleaning force to remove the remaining multi-component fluid from the flexible tip before the outlet closes.

16. The applicator of claim 14, wherein the flexible tip is configured to transition from the dispensing state and the non-dispensing state multiple times such that multi-component fluids are dispensed through the outlet, cleaned from the flexible tip, and again dispensed through the outlet.

17. The applicator of claim 14, wherein the flexible tip is configured and dimensioned to substantially occupy the mixing volume when the restriction member is extended over the flexible tip.

18. The applicator of claim 14, wherein the spring is one of a coiled spring, a leaf spring, and an elastomeric material.

19. The applicator of claim 14, wherein the chamber coupler and flexible tip are configured to slide from a first position to a second position upon compression of the spring.

20. The applicator of claim 14, wherein the chamber coupler and flexible tip are configured to slide from a first position to a second position upon compression of the spring.

* * * * *